US010864549B2

United States Patent
Choi et al.

(10) Patent No.: US 10,864,549 B2
(45) Date of Patent: Dec. 15, 2020

(54) HALF-COATING METHOD FOR NANOPARTICLES

(71) Applicant: Sogang University Research Foundation, Seoul (KR)

(72) Inventors: Jeong Woo Choi, Seoul (KR); Jin Ho Yoon, Seoul (KR); Sang Uk Kim, Seoul (KR)

(73) Assignee: Sogang University Research Foundation, Seoul (KR)

( * ) Notice: Subject to any disclaimer, the term of this patent is extended or adjusted under 35 U.S.C. 154(b) by 72 days.

(21) Appl. No.: 16/085,891

(22) PCT Filed: Feb. 15, 2017

(86) PCT No.: PCT/KR2017/001672
§ 371 (c)(1),
(2) Date: Sep. 17, 2018

(87) PCT Pub. No.: WO2017/159998
PCT Pub. Date: Sep. 21, 2017

(65) Prior Publication Data
US 2019/0118218 A1 Apr. 25, 2019

(30) Foreign Application Priority Data
Mar. 17, 2016 (KR) .................. 10-2016-0032283

(51) Int. Cl.
| | |
|---|---|
| *B05D 3/10* | (2006.01) |
| *C12Q 1/6818* | (2018.01) |
| *B22F 1/00* | (2006.01) |
| *C09D 7/00* | (2018.01) |
| *B22F 1/02* | (2006.01) |
| *B82Y 30/00* | (2011.01) |
| *B82Y 40/00* | (2011.01) |
| *B82Y 5/00* | (2011.01) |

(52) U.S. Cl.
CPC ............ *B05D 3/107* (2013.01); *B05D 3/104* (2013.01); *B22F 1/0018* (2013.01); *B22F 1/02* (2013.01); *C09D 7/00* (2013.01); *C12Q 1/6818* (2013.01); *C12Y 301/00* (2013.01); *B82Y 5/00* (2013.01); *B82Y 30/00* (2013.01); *B82Y 40/00* (2013.01)

(58) Field of Classification Search
CPC .......... C12Q 1/6818; B05D 3/107; B22F 1/02
See application file for complete search history.

(56) References Cited

U.S. PATENT DOCUMENTS

| | | | | |
|---|---|---|---|---|
| 5,298,428 A | * | 3/1994 | O'Rourke ............ | G01N 21/631 356/326 |
| 2010/0233270 A1 | | 9/2010 | Mirkin et al. | |
| 2010/0323906 A1 | * | 12/2010 | Chen .................... | C12Q 1/6827 506/9 |
| 2011/0294685 A1 | * | 12/2011 | O'Halloran .......... | C12Q 1/6825 506/9 |

FOREIGN PATENT DOCUMENTS

KR 10-2015-0003617 A 1/2015

OTHER PUBLICATIONS

Hou et al, MicroRNA detection using lateral flow nucleic acid strips with gold nanoparticles, 2012, Talanta 99, 375-379 (Year: 2012).*
Lee et al, Evidence of Impurities in Thiolated Single-Stranded DNA Oligomers and Their Effect on DNA Self-Assembly on Gold, 2005, Langmuir, 21, 5134-5141 (Year: 2005).*
Ahern, Biochemical, Reagents Kits Offer Scientists Good Return on Investment, 1995, The Scientist, 20, pp. 1-7. (Year: 1995).*
Utelbayev et al, Some Concepts about Substance, Chemical Compound and an Element, 2014, American Chemical Science Journal, 4, 166-173. (Year: 2014).*
Campbell et al , Locked vs. unlocked nucleic acids (LNA vs. UNA): contrasting structures work towards common therapeutic goals, 2011, Chem. Soc. Rev., 40, 5680-5689 (Year: 2011).*
Lee, et al. (2014) "Bioprocessing Device Composed of Protein/DNA/Inorganic Material Hybrid.", *Adv. Funct. Mater*, vol. 24, pp. 1781-1789.
Pei, et al. (2012) "Designed Diblock Oligonucleotide for the Synthesis of Spatially Isolated and Highly Hybridizable Functionalization of DNA-Gold Nanoparticle Nanoconjugates.", *Journal of the American Chemical Society*, 2012, vol. 134, pp. 11876-11879.
Tan, et al. (2014) "DNA as a powerful tool for morphology control, spatial positioning, and dynamic assembly of nanoparticles.", *Acc. Chem. Res.*, vol. 47, pp. 1881-1890.
International Search Report (ISR) from corresponding International Patent Application No. PCT/KR2017/001672, dated Feb. 15, 2017, with an English translation.

* cited by examiner

*Primary Examiner* — Narayan K Bhat
(74) *Attorney, Agent, or Firm* — Harness, Dickey & Pierce, P.L.C.

(57) ABSTRACT

The present invention provides a method and a kit for half coating nanoparticles. According to the present invention, nanoparticles can be half coated in a relatively simple and economical process that can replace complicated processes, such as chemical synthesis, of a conventional Janus nanoparticle-preparing method.

18 Claims, 9 Drawing Sheets

Specification includes a Sequence Listing.

(a)

(b)

```
SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: ssDNA1

<400> SEQUENCE: 1
ataaaaaaaa cgcgggggtt ccgcg                                25

<210> SEQ ID NO 2
<211> LENGTH: 25
<212> TYPE: DNA
<213> ORGANISM: Artificial Sequence
<220> FEATURE:
<223> OTHER INFORMATION: ssDNA2

<400> SEQUENCE: 2
gcgcccccaa ggcgcaaaaa taaaa                                25

<210> SEQ ID NO 3
<211> LENGTH: 25
<212> TYPE: DNA
<213> ORGANISM: Artificial Sequence
<220> FEATURE:
<223> OTHER INFORMATION: DNA_Sample

<400> SEQUENCE: 3
ataaaaaaaa cgcgggggtt ccgcg                                25
```

HALF-COATING METHOD FOR NANOPARTICLES

CROSS-REFERENCE TO RELATED APPLICATIONS

This application is a national phase application of PCT Application No. PCT/KR2017/001672, filed on Feb. 15, 2017, which claims the benefit and priority to Korean Patent Application No. KR10-2016-0032283, filed Mar. 17, 2016. The entire disclosures of the applications identified in this paragraph are incorporated herein by references.

TECHNICAL FIELD

The present invention was made with the support of the Ministry of Science, ICT, and Future Planning of the Republic of Korea, under Project No. 201633021.01, which was conducted under the research subject named "Research Center for Disease Biophysics of Sogang-Harvard" within the research project entitled "Global R&D Center" by Sogang University under the management of the National Research Foundation of Korea, from 1 Sep. 2016 to 31 Aug. 2017.

The present invention was made with the support of the Ministry of Science, ICT, and Future Planning of the Republic of Korea, under Project No. 201631046.01, which was conducted under the research subject named "Basal ganglia-on-a-chip for drug screening of brain disease based on nanostructure" within the research project entitled "Middle-Grade Researcher Supporting Program" by Sogang University under the management of the National Research Foundation of Korea, from 1 Nov. 2016 to 31 Oct. 2017.

The present invention was made with the Ministry of Education of the Republic of Korea, under Project No. 201721001.01, which was conducted under the research subject entitled "Development of Nanobiochip Platform to Analyze Drug Evaluation in Brain Disease" within the research project named "Key Research Institute Program" by Sogang University under the management of the National Research Foundation of Korea, from 1 Jan. 2017 to 31 Dec. 2017.

The present invention relates to a method for half-coating of nanoparticles.

BACKGROUND

Nanoparticles are generally particles having a size of 1-100 nm. In terms of nanotechnology, nanoparticles are per se defined as carriers or defined as ones performing particular functions. Nanoparticles, when compared with larger particles formed of the same components, can exhibit greater activity in various kinds of reactions due to a dramatically increased surface area thereof, and thus serve as a catalytic agent. In addition, as the size of nanoparticles decreases, the nanoparticles localize electrons and induce a quantum effect, and thus may have physical or optical features that they did not have before. Furthermore, nanoparticles can be utilized for light emitting devices and the like on the basis of their size since the light energy that can emit light varies according to the size of the nanoparticles.

A field of interest for nanoparticles is the field of biology among the many fields in which nanoparticles can be applied. In general, living organisms are composed of cells equal to or smaller than 10 µm. Moreover, the constituents of the cells may be composed at the nanometer level. In studies of such intracellular constituents or at cellular levels, nanoparticles having suitable sizes can be variously utilized in drug or gene delivery, pathogen detection, intracellular labeling, cancer cell necrosis, or the like.

In recent years, Janus nanoparticles, which have an asymmetric structure and are formed of different surface materials, have received great attention. Janus nanoparticles are nanoparticles having a surface formed of different materials, so one nanoparticle can have two different types of characteristics. For example, one half of the Janus nanoparticle may have a hydrophilic characteristic and the other half may have a hydrophobic characteristic. However, the manufacture of such a Janus nanoparticle requires very complicated procedures. Self-assembly based on a block copolymer, masking of different materials, and the like are representative methods that are used in the manufacturing of Janus nanoparticles. These methods require the understanding of all thermodynamic characteristics of the block copolymers and factors affecting self-assembly, and have limitations in that several devices and complicated procedures are needed.

SUMMARY

Technical Problem

The present inventors endeavored to develop a method for partial coating of nanoparticles by using a biomaterial. As a result, the present inventors produced half-coated nanoparticles by immobilizing nanoparticles on a substrate using DNA and coating an exposed surface thereof, and thus completed the present invention.

Therefore, an aspect of the present invention is to provide a method for half-coating of nanoparticles.

Another aspect of the present invention is to provide a kit for half-coating of nanoparticles.

Technical Solution

In accordance with an aspect of the present invention, there is provided a method for half-coating of nanoparticles, the method including:

(a) self-assembling a first oligonucleotide on a substrate;

(b) hybridizing a second oligonucleotide, complementary to a terminal region of the first oligonucleotide, with the first oligonucleotide;

(c) conjugating nanoparticles to the second oligonucleotide;

(d) coating an exposed surface of the nanoparticles; and (e) treating the product in step (d) with DNA nuclease to obtain half-coated nanoparticles.

The present inventors endeavored to develop a method for partial coating of nanoparticles by using a biomaterial. As a result, the present inventors produced half-coated nanoparticles by immobilizing nanoparticles on a substrate using DNA and coating an exposed surface thereof.

The method for half-coating of nanoparticles of the present invention may be used in the manufacturing of Janus nanoparticles.

As used herein, the term "Janus nanoparticles (or Janus particles)" refers to a form of nanoparticles having two or more distinct physical characteristics on a surface of the nanoparticles. The Janus nanoparticles are particles that have distinctive characteristics associated with an asymmetric structure and/or functionalization thereof. Conventional methods for manufacturing the Janus nanoparticles employ: (a) masking; (b) self-assembly by a block copolymer; (c) self-assembly by competitive adsorption; and (d) phase separation.

The conventional methods for manufacturing nanoparticles have a disadvantage in that complicated procedures, such as chemical synthesis, are needed.

The method for half-coating of nanoparticles of the present invention will be described in detail step by step.

Step (a): Self-Assembly of First Oligonucleotide

A first oligonucleotide is immobilized on a substrate.

According to an embodiment of the present invention, the substrate is formed of a metal, a metal oxide, glass, a ceramic, quartz, silicon, a semiconductor, a Si/SiO2 wafer, germanium, gallium arsenide, carbon, carbon nanotubes, a polymer, Sepharose or agarose.

According to another embodiment of the present invention, the substrate is formed of a metal, a metal oxide, glass or a ceramic.

According to a particular embodiment of the present invention, the substrate is formed of a metal.

As verified in the examples below, the substrate is a gold substrate.

One of the main features of the present invention is that nanoparticles are immobilized on a substrate through a biomaterial before the nanoparticles are coated.

In the present invention, for the immobilization of nanoparticles on a substrate, an oligonucleotide is used.

As used herein, the term "oligonucleotide" refers to a linear oligomer of natural or modified monomers or linkages.

The oligonucleotide includes a deoxyribonucleotide and a ribonucleotide, which are capable of specifically hybridizing with a target nucleotide sequence, and exist naturally or are artificially synthesized.

The oligonucleotide is preferably a single chain for maximal efficiency in hybridization. Preferably, the oligonucleotide is an oligodeoxyribonucleotide.

The oligonucleotide of the present invention may include naturally occurring dNMPs (i.e., dAMP, dGMP, dCMP and dTMP), or nucleotide analogs or derivatives. Also, the oligonucleotide may include a ribonucleotide.

The first oligonucleotide is bound and self-assembled on the substrate via a thiol group introduced into the 5'-terminal thereof.

As used herein, the term "self-assembly" means that randomly existing constituents spontaneously form an organized structure or shape by an interaction between the constituents without external instruction.

That is, the first oligonucleotide forms a spontaneous structure on the substrate by an interaction therebetween.

The oligonucleotide used in the half-coating of nanoparticles of the present invention has such a length that the oligonucleotide can be self-assembled on the substrate and can hybridize with another oligonucleotide.

According to an embodiment of the present invention, the first oligonucleotide is 10-100 bp (base pair) in length.

According to another embodiment, the first oligonucleotide is 10-80 bp, 10-60 bp, 10-40 bp or 10-30 bp in length.

As the first oligonucleotide used in half-coating of the nanoparticles of the present invention, any sequence can be used. The reason is that the DNA nuclease used in the present invention is not a restriction enzyme that recognizes and cleaves a particular sequence, but an enzyme that recognizes and cleaves single-stranded DNA or double-stranded DNA. Therefore, any sequence can be used as the DNA nuclease.

According to an embodiment of the present invention, the first oligonucleotide has a nucleotide sequence of SEQ ID NO: 1.

Step (b): DNA Hybridization

Then, a second oligonucleotide complementary to a terminal region of the first oligonucleotide is hybridized.

According to an embodiment of the present invention, the terminal region is a 3'-terminal region or a 5'-terminal region.

According to another embodiment of the present invention, the terminal region is a 3'-terminal region.

The second oligonucleotide in step (b) has an appropriate length such that one terminal region of the second oligonucleotide partially hybridizes with the first oligonucleotide and the other terminal region thereof is conjugated to a nanoparticle.

According to an embodiment of the present invention, the second oligonucleotide is 10-100 bp in length.

According to another embodiment, the second oligonucleotide is 10-80 bp, 10-60 bp, 10-40 bp, or 10-30 bp in length.

The first oligonucleotide in step (a) and the second oligonucleotide in step (b) have partially complementary sequences, respectively.

According to an embodiment of the present invention, the first oligonucleotide and the second oligonucleotide have complementary sequences at 3'-terminal regions thereof, respectively.

As used herein, the term "complementary" refers to being sufficiently complementary such that the second oligonucleotide selectively hybridizes with the first oligonucleotide under certain annealing conditions or strict conditions. The term is meant to encompass all of "substantially complementary" and "perfectly complementary", and preferably means being perfectly complementary.

According to an embodiment of the present invention, the second oligonucleotide hybridizes with a terminal region of the first oligonucleotide by 5-80 bp in length.

According to another embodiment of the present invention, the second oligonucleotide hybridizes with the terminal region of the first oligonucleotide by 5-60 bp, 5-40 bp, 5-30 bp, or 5-20 bp in length.

As the second oligonucleotide used in the half-coating of nanoparticles of the present invention, any sequence that partially hybridizes with the first oligonucleotide can be used.

According to an embodiment of the present invention, the second oligonucleotide has a nucleotide sequence of SEQ ID NO: 2.

It is designed such that the nucleotide sequences at the site in which the first oligonucleotide and the second oligonucleotide hybridize with each other have a GC content of 80% or more, for stable hybridization.

As used herein, the term "hybridization" means that complementary single-stranded nucleic acids form a double-stranded nucleic acid. The hybridization may occur when the degree of complementarity between two stands of nucleic acids is completed (perfectly matched) or even when some mismatch nucleotides are present. The degree of complementarity required for hybridization may vary depending on the hybridization conditions, and may be controlled by, particularly, the temperature.

Step (c): Immobilization of Nanoparticles

Then, nanoparticles are conjugated to the second oligonucleotide.

The conjugation of the second oligonucleotide and the nanoparticle may be any conjugation of a nucleic acid and a nanoparticle, which is known in the art. For example, a conjugation through gold-thiol binding between a gold nanoparticle and a thiol group introduced into a terminal of an oligonucleotide, a conjugation through a nickel nanoparticle and a histidine group, a conjugation through a silver nanoparticle and a thiol group, or a conjugation through linking of a nanoparticle and a particular functional group may be applied.

According to an embodiment of the present invention, the nanoparticles are conjugated via a thiol group introduced into a terminal of the second oligonucleotide.

The nanoparticles that are applied to half-coating of the nanoparticles of the present invention may be any nanoparticles.

According to an embodiment of the present invention, the nanoparticle is a metal nanoparticle, a metal oxide nanoparticle, or an alloy nanoparticle, and a semiconductor nanoparticle.

Step (d): Coating

Then, an exposed surface of the nanoparticles is coated. The coating may be any coating that is known in the art. For example, the coating may be conducted under any conditions that do not affect the structure of the first oligonucleotide self-assembled on the substrate, the second oligonucleotide partially hybridized with the first oligonucleotide, and the nanoparticle conjugated to the second oligonucleotide.

As validated in the examples below, a chemical material is coated on the exposed surface of the nanoparticles in step (d).

Step (e): Treatment with DNA Nuclease

Lastly, the product in step (d) is treated with DNA nuclease to obtain half-coated nanoparticles.

The other of the main features of the present invention is that DNA nuclease, a biomaterial, is used for half-coating of nanoparticles.

As used herein, the term "DNA nuclease" is an enzyme that cleaves phosphodiester bonds between nucleotide subunits in nucleic acids.

As the DNA nuclease used in the present invention, any DNA nuclease known in the art may be used. The DNA nuclease may be any DNA nuclease that cleaves oligonucleotides that link nanoparticles and a substrate.

According to an embodiment of the present invention, DNA nuclease is single-stranded DNA nuclease or double-stranded DNA nuclease.

According to another embodiment of the present invention, the DNA nuclease is single-stranded DNA nuclease.

According to a particular embodiment of the present invention, the DNA nuclease is Mungbean nuclease, *Aspergillus* nuclease S1, P1 nuclease or BAL 31 nuclease.

As validated in the examples below, half-coated nanoparticles are obtained by treatment with the DNA nuclease.

In accordance with another aspect of the present invention, there is provided a kit for half-coating of nanoparticles, the kit including: (a) a substrate; (b) a first oligonucleotide self-assembled on the substrate; (c) a second oligonucleotide partially hybridized with a terminal of the first oligonucleotide; and (d) DNA nuclease.

Since the kit of the present invention uses the method for half-coating of nanoparticles, descriptions of overlapping contents between the two inventions will be omitted to avoid excessive complication of the specification.

Advantageous Effects

Features and advantages of the present invention are summarized as follows.

(a) The present invention provides a method and kit for half-coating of nanoparticles.

(b) The present invention can substitute complicated procedures, such as chemical synthesis, in the conventional method for manufacturing Janus nanoparticles.

(c) The present invention enables half-coating of nanoparticles through a comparatively simple and economical method.

BRIEF DESCRIPTION OF THE DRAWINGS

FIG. 1a shows the results of electrophoresis of DNA reacted with mungbean nuclease, and FIG. 1b shows the results confirming the hydrolytic degradation of mungbean nuclease using fluorescence-linked DNA.

FIGS. 4a and 4b are TEM images of a mungbean nuclease control group, and an experimental group in which gold nanoparticles immobilized on a substrate by DNA and then half-coated with a chemical substance complex were treated with mungbean nuclease, respectively. FIG. 4c shows the absorbance measurement results of the control group and the experimental group.

DETAILED DESCRIPTION

Hereinafter, the present invention will be described in detail with reference to examples. These examples are only for illustrating the present invention more specifically, and it will be apparent to those skilled in the art that the scope of the present invention is not limited by these examples.

EXAMPLE 1

Confirmation of Mungbean Nuclease Functions

An experiment to investigate whether mungbean nuclease degraded single-stranded DNA was conducted. Two methods using electrophoresis and fluorescence analysis were used for the investigation.

First, 20 bp-sized single-stranded DNA samples (CCCACATTTACTTATGATCC) (SEQ ID NO:3) were prepared, and subjected to an electrophoresis experiment. Mungbean nuclease (New England BioLabs) was in a concentration state of 10000 unit/Ml, and thus was diluted with a reaction buffer (Mungbean nuclease reaction buffer: 30 mM NaCl, 50 mM sodium acetate, 1 mM ZnSO4, pH 5.0, 25° C.) to a state of 2 unit, followed by reaction. The standard for 1 unit defines the amount of an enzyme required to degrade 1 µg of DNA at 37° C. The reaction of mungbean nuclease and DNA was conducted in an incubator at 37° C. after 100 µl of 10 µM DNA and 2 units of mungbean nuclease dissolved in the mungbean nuclease reaction buffer was placed in a 1.5 Ml-tube.

Thereafter, electrophoresis was conducted on an agarose gel at 100 V for 1 hour, and bands were stained with SYBR gold. The electrophoresis results could confirm that the DNA samples reacted with mungbean nuclease showed no bands since DNA was degraded (lanes 2-6 and 9 in FIG. 1a).

Thereafter, the samples where the fluorescent substance cy5 and the quencher BHQ2 were attached to both ends of the single-stranded DNA were subjected to a fluorescent experiment. The size of the used single-stranded DNA was 20 bp, that is, about 7 nm in length, and it could be confirmed that due to a quenching effect, fluorescence was not shown when cy5 and BHQ2 were linked with DNA therebetween. However, it could be confirmed that, in the samples reacted with mungbean nuclease, DNA was cleaved and cy5 separated from BHQ2, resulting in the intensity of fluorescence. These confirmed a function of mungbean nuclease to degrade DNA.

Figure 1A:
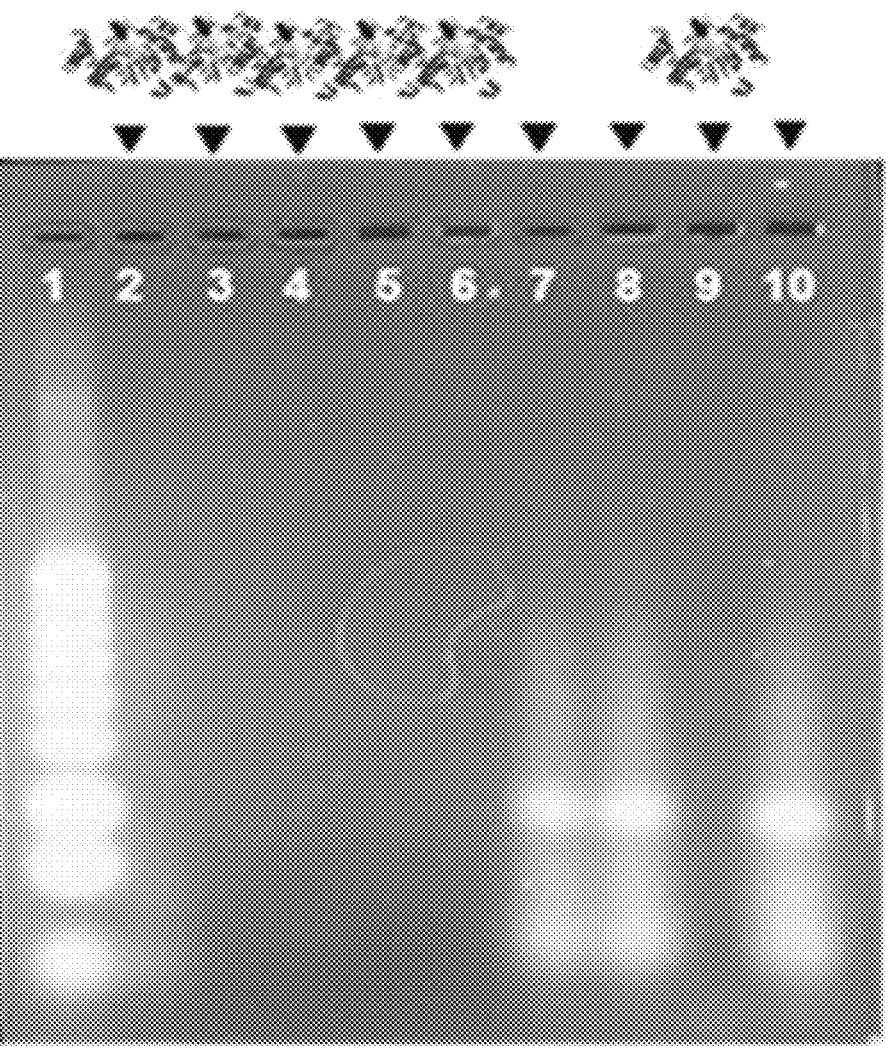
FIGS. 1a and 1b show the results confirming the hydrolytic degradation of mungbean nuclease on single-stranded DNA.
Figure 1B:
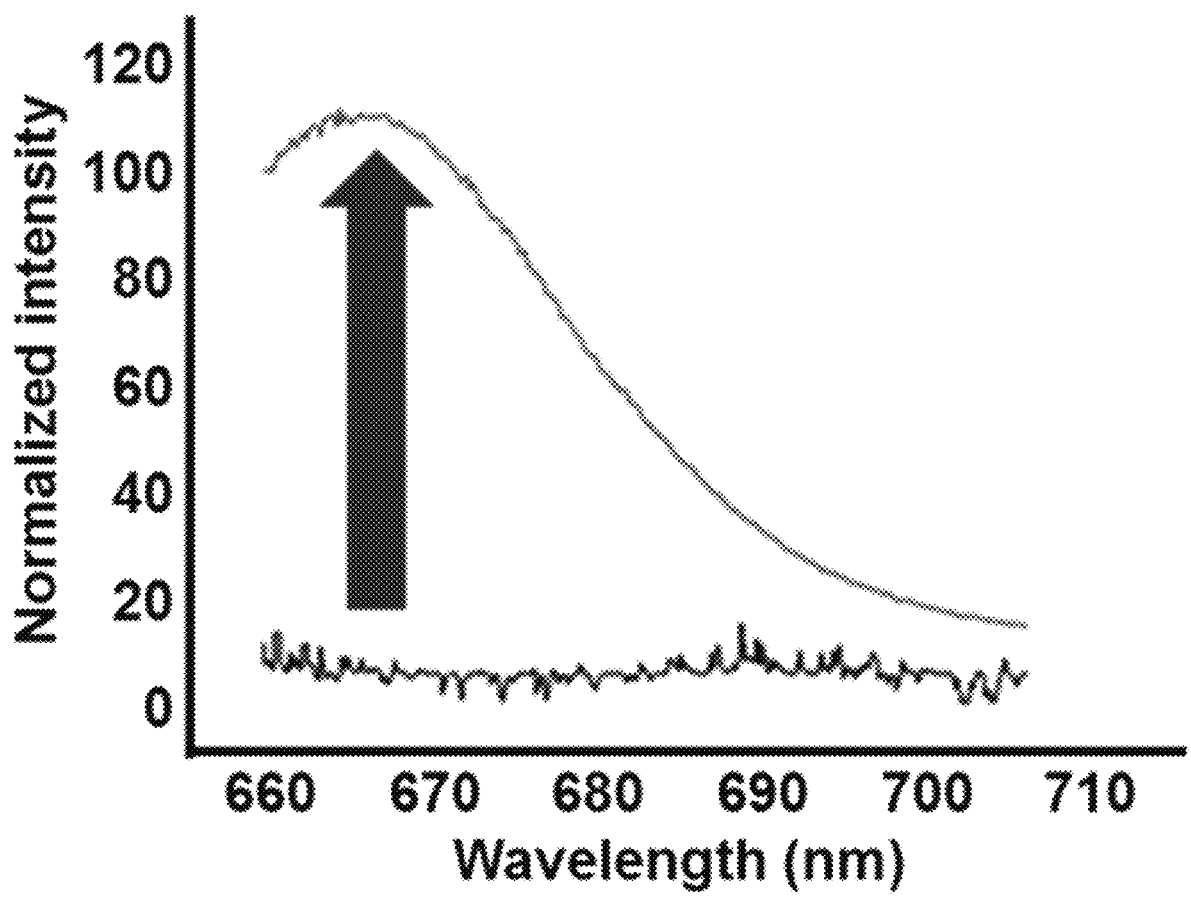

FIG. 1a shows the results of electrophoresis of DNA and DNA reacted with mungbean nuclease, and FIG. 1b is an image showing the results of the fluorescence intensity experiment.

EXAMPLE 2

Confirmation, Through Fluorescence Microscope and SEM, that Gold Nanoparticles, Immobilized on Gold Substrate by DNA, Separated from Gold Substrate After Mungbean Nuclease Treatment For the manufacturing of half-coated gold nanoparticles using mungbean nuclease, gold nanoparticles were first immobilized onto a gold substrate using DNA. As the gold substrate, a substrate with a size of 0.5 mm×0.5 mm in which chrome (5 nm thickness) and gold (20 nm thickness) were deposited on a silicon substrate was used. 20 µl of 100 µM 25-bp-sized first single-stranded DNA with a thiol group attached thereto (SH-ATAAAAAAAACGCGGGGGTTCCGCG, 25 bp, SEQ ID NO: 1; the underlined part corresponds to a sequence complementary to second single-stranded DNA) was immobilized on the gold substrate by self-assembly, and then 20 µl of 10 µM 25-bp-sized second single-stranded DNA with a thiol group attached thereto (GCGCCCC-CAAGGCGCAAAAATAAAA-SH, 25 bp, SEQ ID NO: 2; the underlined part corresponds to a sequence complementary to first single-stranded DNA), which was partially complementary to the first single-stranded DNA, was placed thereon, followed by reaction for 3 hours, thereby forming double-stranded DNA. By shortening a portion where a double strand is formed by complementary bonding of the first DNA and the second DNA, each of the rest DNA sequence portions was present in a single strand state so as to be degraded by mungbean nuclease. The complementary DNA of the immobilized DNA sequence is designed to have a thiol group at the end of the upturned portion after the formation of a double strand, allowing immobilization of a gold nanoparticle. Thereafter, the immobilization of 20 nm-sized gold nanoparticles was conducted for 3 hours. Thus, the second DNA as the complementary DNA was immobilized to a lower portion of the gold nanoparticle through Au—S reaction, and user desired substances were immobilized to an upper portion of the gold nanoparticle.

For the investigation of whether the gold nanoparticles immobilized on the gold substrate by the first DNA and the second DNA separated from the gold substrate due to mungbean nuclease, the cy3 fluorescent substance with a thiol group attached thereto was immobilized onto an upper portion of the gold nanoparticles, immobilized to the gold substrate by DNA, for 3 hours. After the sample thus prepared was observed by a fluorescence microscope, the sample was reacted with a solution containing mungbean nuclease in an incubator at 37° C. for 1 hour, and then the sample was observed by the fluorescence microscope.

Figure 2A:
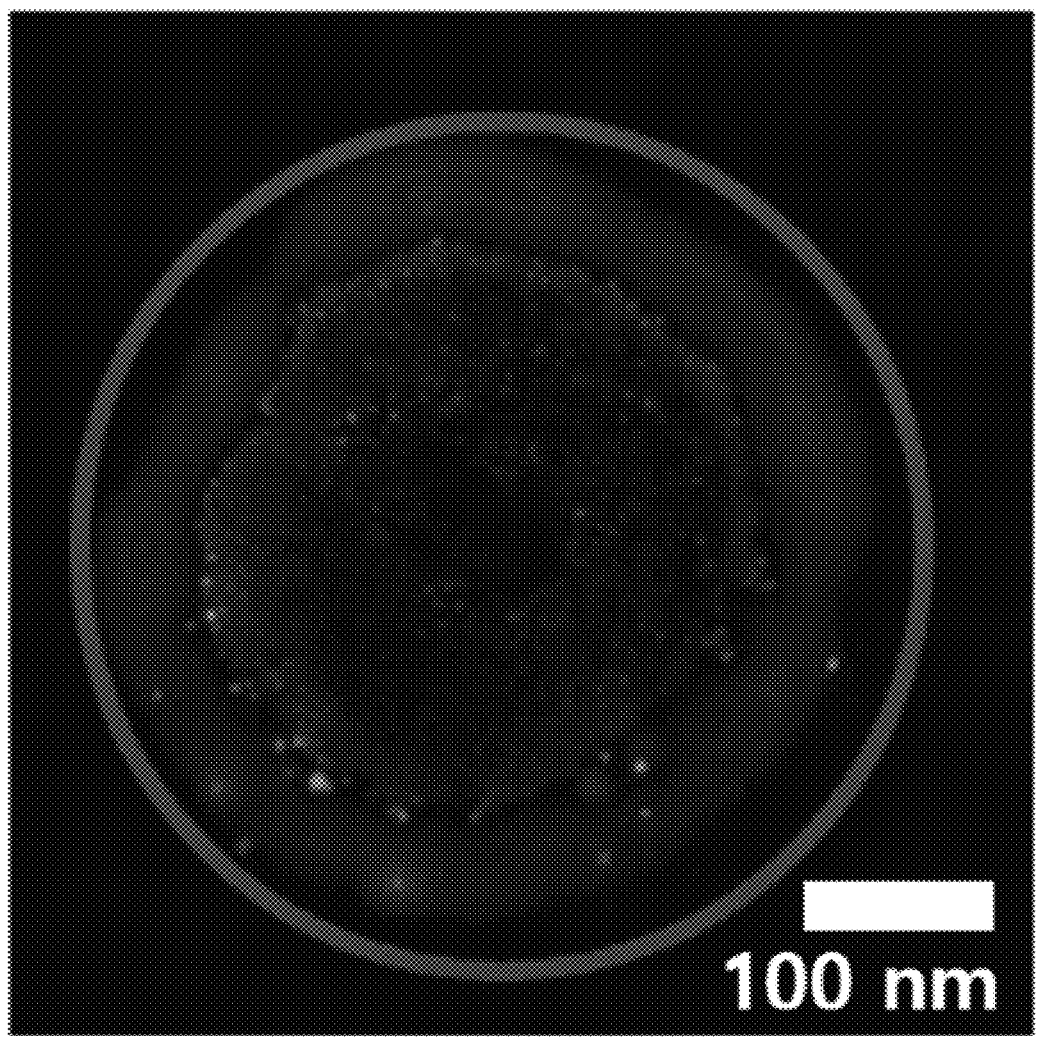
FIGS. 2a and 2b are fluorescence images showing the results of mungbean nuclease treatment on a gold nanoparticle, immobilized on a substrate by DNA. Fluorescence images before (2a) and after (2b) mungbean nuclease treatment on the gold nanoparticle with a fluorescent dye attached thereto are shown.
Figure 2B:
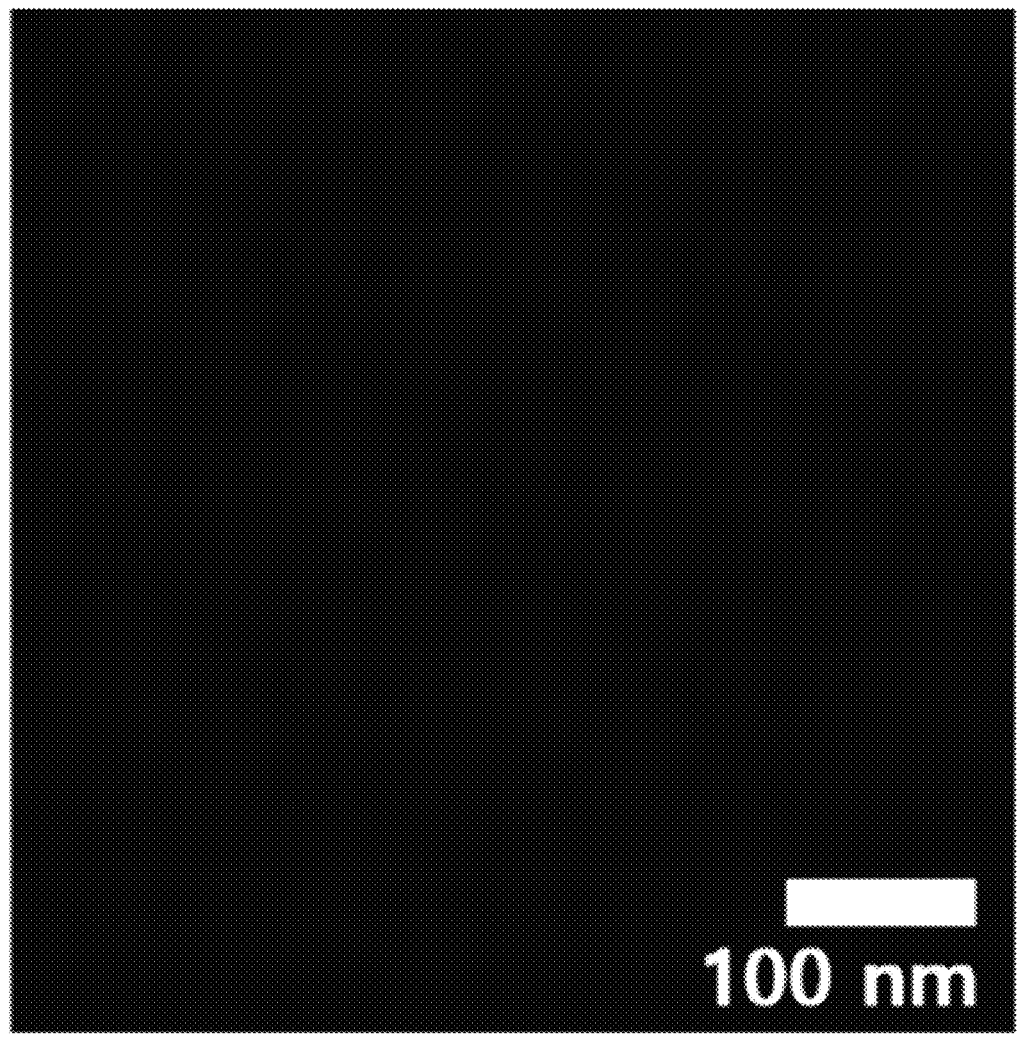

FIGS. 2a and 2b are an image (2a) showing the fluorescence of cy3 attached to the gold nanoparticle immobilized on the gold substrate through DNA, and a fluorescence image (2b) showing the gold substrate wherein the sample was reacted with mungbean nuclease to degrade DNA and thus the gold nanoparticle with cy3 fluorescence attached thereto separated from the gold substrate, resulting in fluorescence disappearance.

Thereafter, the substrates subjected to the same experiment as above were observed by SEM. As a result of SEM observation of the gold substrate before mungbean nuclease treatment, it could be confirmed that gold nanoparticles were densely immobilized on the gold substrate, but after the reaction with mungbean nuclease, most of the gold nanoparticles separated and disappeared.

Figure 3A:
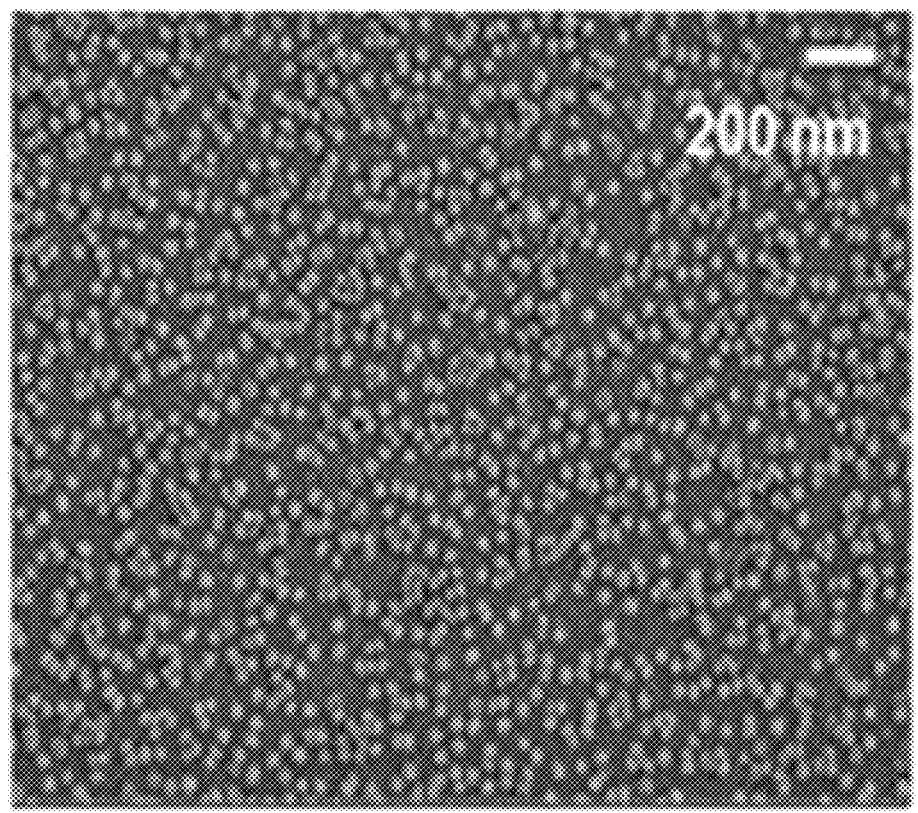
FIGS. 3a and 3b are SEM images showing the results of mungbean nuclease treatment on gold nanoparticles, immobilized on a substrate by DNA. SEM images before (3a) and after (3b) mungbean nuclease treatment are shown.
Figure 3B:
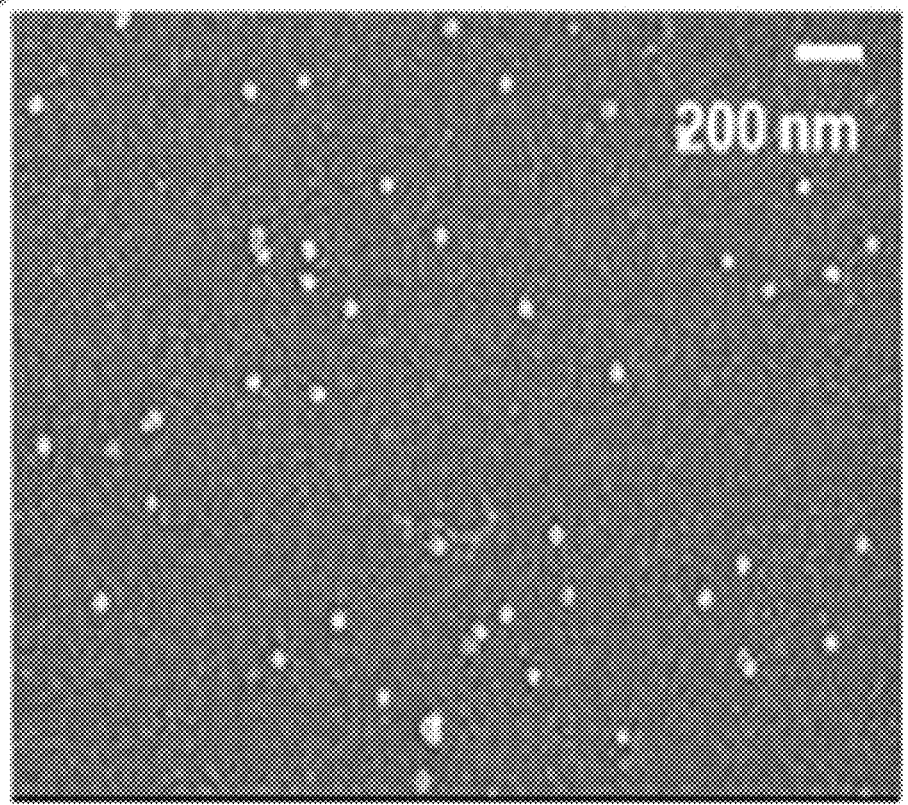

FIGS. 3a and 3b are a SEM image (3a) showing gold nanoparticles immobilized on the gold substrate through DNA and an image (3b) showing that gold nanoparticles disappeared after the reaction with Mungbean nuclease.

EXAMPLE 3

Confirmation, Through TEM and UV-Vis, of Half-Coated Gold Nanoparticles Separated by Mungbean Nuclease For the investigation of half-coated gold nanoparticles, which separated from a gold substrate by mungbean nuclease, the immobilization of gold nanoparticles on a gold substrate using DNA was first conducted by the method presented above. Thereafter, a chemical substance complex with a thiol group was immobilized on the gold nanoparticles for 3 hours. The chemical substance complex was composed of cucurbit [8] Uril (CB), Trp-Gly-Gly (WGG peptide), and 5,5'-Bis(mercaptomethyl)-2,2'-bipyridine, and prepared by self-assembly. The sample thus prepared was allowed to react with a solution containing mungbean nuclease in an incubator at 37° C. for 1 hour. Thereafter, the sample was taken out from the solution, and then the solution was observed by EF-TEM. As a result of EF-TEM analysis of the solution before the sample was placed therein, it could be confirmed that only mungbean nuclease was present. However, it could be confirmed that, in the solution obtained after the sample was immersed in the solution to react with the solution for 1 hour in an incubator and then taken out, the gold nanoparticles, separating from the gold substrate, and the chemical substance complex, half-coated on the gold nanoparticles, were observed, together with mungbean nuclease. Thereafter, as a result of UV-vis analysis of the two solutions, the peaks slightly increased near 250 nm and 270 nm, which indicate the gold nanoparticle and the chemical substance half-coated on the nanoparticle, compared with the peak of the solution containing only mungbean nuclease, and through these results could confirm the separation of half-coated gold nanoparticles.

Figure 4A:
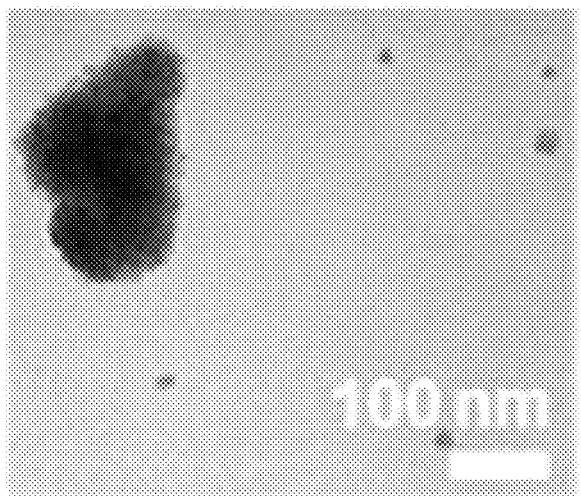
FIGS. 4a, 4b and 4c show the results confirming half-coated gold nanoparticles.
Figure 4B:
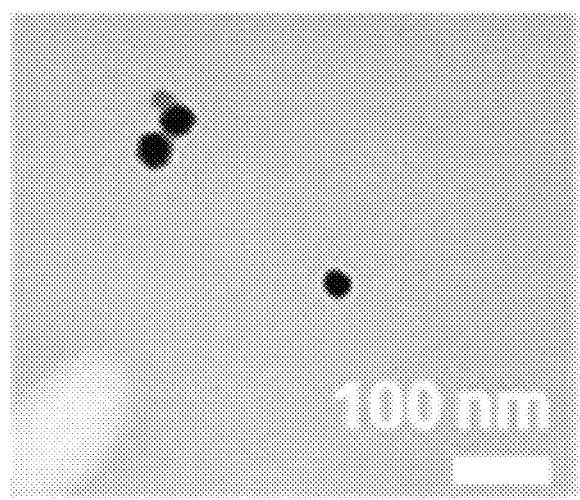
Figure 4C:
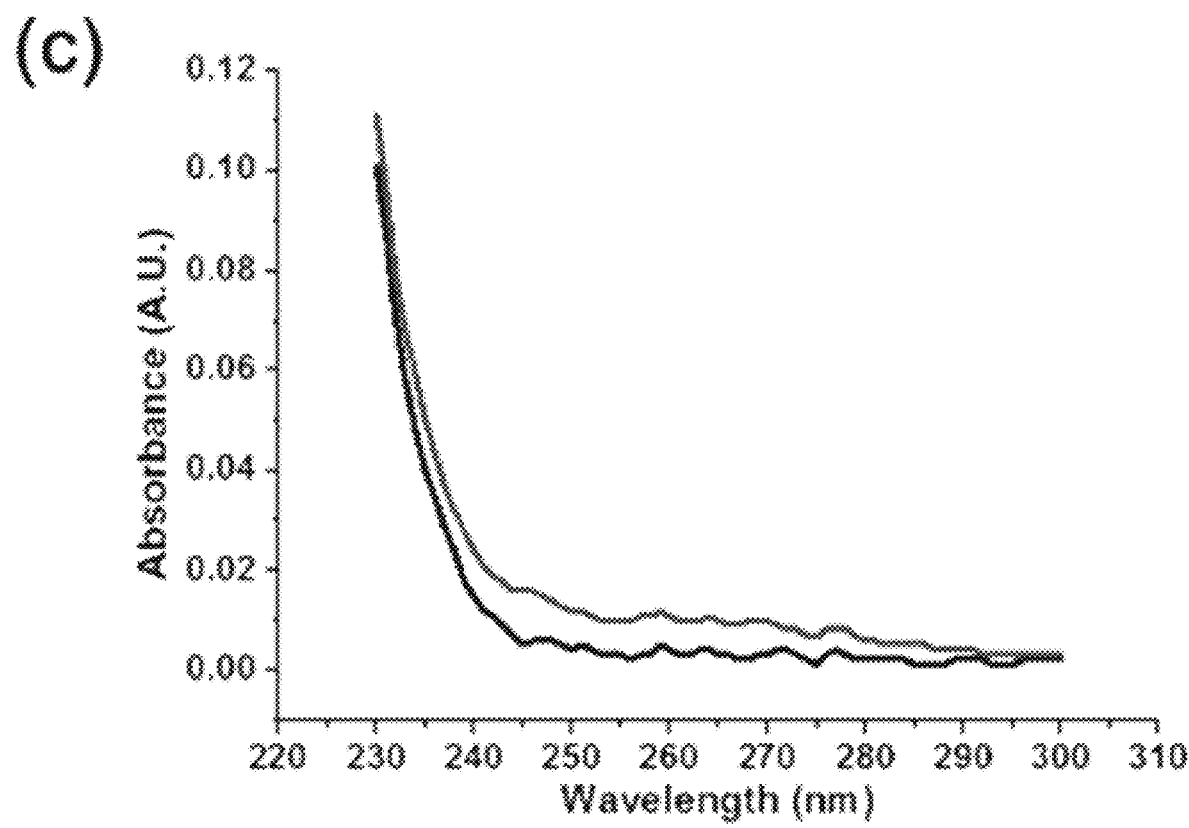

FIGS. 4a to 4b are TEM images of (4a) the solution containing only mungbean nuclease, and (4b) the solution obtained after the substrate, obtained by immobilizing the gold nanoparticles on the gold substrate using DNA and immobilizing the chemical substance complex on the gold nanoparticles, was immersed in the solution to react with the solution. FIG. 4c shows UV-vis measurement results of the two solutions above.

Figure 5:
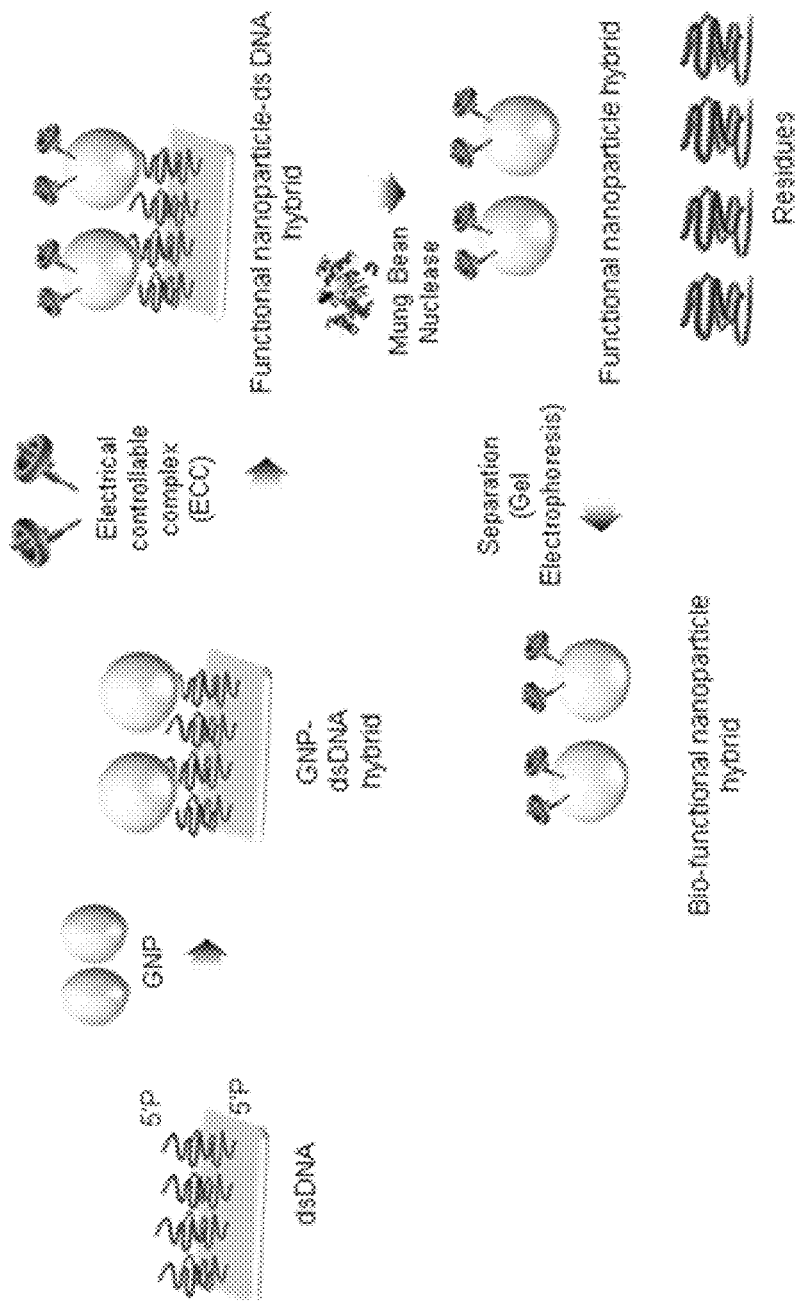
FIG. 5 schematically shows a method for half-coating of nanoparticles of the present invention.

FIG. 5 schematically shows a method for half-coating of nanoparticles of the present invention. In FIG. 5, DNAs were immobilized on a gold substrate, gold nanoparticles were immobilized thereon, an electrical controllable complex cucurbit [8] Uril (CB), Trp-Gly-Gly (WGG peptide) and 5,5'-bis(mercaptomethyl)-2,2'-bipyridine) was immobilized thereon by bonding, and thereafter, DNAs were degraded through the reaction with mungbean nuclease, so that gold nanoparticles half-coated with cucurbit [8] Uril (CB), Trp-Gly-Gly (WGG peptide), and 5,5'-Bis(mercaptomethyl)-2,2'-bipyridine separated from the substrate.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A kit comprising:
   (a) a substrate;
   (b) a first oligonucleotide self-assembled on the substrate;
   (c) a second oligonucleotide partially hybridized with a terminal of the first oligonucleotide;
   (d) single-stranded DNA nuclease or a double-stranded DNA nuclease; and
   (e) nanoparticles half-coated with a chemical substance complex, wherein the chemical substance complex is cucibit [8] Uril (CB), Trp Gly Gly (WGG peptide), and 5,5'Bis(mercaptomethyl)-2,2'-bipyridine.

2. The kit of claim 1, wherein the substrate is formed of a metal, a metal oxide, glass, a ceramic, quartz, silicon, a semiconductor, a Si/SiO2 wafer, germanium, gallium arsenide, carbon, carbon nanotubes, a polymer, Sepharose, or agarose.

3. The kit of claim 1, wherein the first oligonucleotide is 10-100 bp (base pair) in length.

4. The kit of claim 1, wherein the terminal of the first oligonucleotide is 3'-terminal or 5'-terminal.

5. The kit of claim 1, wherein the second oligonucleotide is 10-100 bp (base pair) in length.

6. The kit of claim 1, wherein the second oligonucleotide is hybridized with a terminal region of the first oligonucleotide by a length of 5-80 bp.

7. The kit of claim 1, wherein the nanoparticles are conjugated via a thiol group introduced into the terminal of the second oligonucleotide.

8. The kit of claim 1, wherein the nanoparticles include metal nanoparticles, metal oxide nanoparticles, alloy nanoparticles, and semiconductor nanoparticles.

9. The kit of claim 1, wherein the DNA nuclease is Mungbean nuclease, *Aspergillus* nuclease S1, P1 nuclease, or BAL 31 nuclease.

10. A method for half-coating of nanoparticles, the method comprising:
    (a) self-assembling a first oligonucleotide on a substrate;
    (b) hybridizing a second oligonucleotide, complementary to a terminal region of the first oligonucleotide, with the first oligonucleotide;

(c) conjugating nanoparticles to the second oligonucleotide;
(d) coating an exposed surface of the nanoparticles with cucibit [8] Uril (CB), Trp Gly Gly (WGG peptide) and 5,5'Bis(mercaptomethyl)-2,2'-bipyridine; and
(e) treating the product in step (d) with single-stranded DNA nuclease or a double-stranded DNA nuclease to obtain half-coated nanoparticles.

11. The method of claim 10, wherein the substrate is formed of a metal, a metal oxide, glass, a ceramic, quartz, silicon, a semiconductor, a Si/SiO2 wafer, germanium, gallium arsenide, carbon, carbon nanotubes, a polymer, Sepharose, or agarose.

12. The method of claim 10, wherein the first oligonucleotide is 10-100 bp (base pair) in length.

13. The method of claim 10, wherein the terminal region in step (b) is a 3'-terminal region or a 5'-terminal region.

14. The method of claim 10, wherein the second oligonucleotide in step (b) is 10-100 bp (base pair) in length.

15. The method of claim 10, wherein the second oligonucleotide in step (b) is hybridized with the terminal region of the first oligonucleotide by a length of 5-80 bp.

16. The method of claim 10, wherein the nanoparticles in step (b) are conjugated via a thiol group introduced into a terminal of the second oligonucleotide.

17. The method of claim 10, wherein the nanoparticles in step (c) include metal nanoparticles, metal oxide nanoparticles, alloy nanoparticles, and semiconductor nanoparticles.

18. The method of claim 10, wherein the DNA nuclease is Mungbean nuclease, *Aspergillus* nuclease S1, P1 nuclease, or BAL 31 nuclease.

* * * * *